US00PP27771P2

(12) United States Plant Patent
Lyrene et al.

(10) Patent No.: US PP27,771 P2
(45) Date of Patent: Mar. 14, 2017

(54) BLUEBERRY PLANT NAMED 'FL06-556'

(50) Latin Name: ***Vaccinium corymbosum* L.**
Varietal Denomination: FL06-556

(71) Applicant: Florida Foundation Seed Producers, Inc., Marianna, FL (US)

(72) Inventors: Paul M. Lyrene, Micanopy, FL (US); James W. Olmstead, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/998,938

(22) Filed: Mar. 7, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP12,165 | P2 | 10/2001 | Lyrene |
| PP20,027 | P3 | 5/2009 | Lyrene |
| PP26,312 | P2 | 1/2016 | Lyrene et al. |
| PP26,313 | P2 | 1/2016 | Lyrene et al. |
| PP26,523 | P3 | 3/2016 | Lyrene |
| PP26,679 | P2 | 5/2016 | Lyrene et al. |
| 2015/0237775 | P1 | 8/2015 | Lyrene |
| 2015/0237776 | P1 | 8/2015 | Lyrene |

OTHER PUBLICATIONS

U.S. Appl. No. 14/998,937, filed Mar. 7, 2016, Norden et al.

*Primary Examiner* — June Hwu
(74) *Attorney, Agent, or Firm* — Dentons US LLP

(57) ABSTRACT

'FL06-556' is a new and distinct southern highbush blueberry (*Vaccinium corymbosum* L.) variety distinguished by a low chilling requirement, upright growth habit, and very firm, crisp fruit that are sweet and low acid with a small dry picking scar.

6 Drawing Sheets

Latin name of the genus and species of the plant claimed: *Vaccinium corymbosum* L.

Variety denomination: 'FL06-556'.

BACKGROUND OF THE INVENTION

The present invention relates to a new and distinct hybrid variety of southern highbush blueberry (*Vaccinium corymbosum* L.) named 'FL06-556'. 'FL06-556' is a blueberry clone distinguished by its low chilling requirement, vigorous, upright bush habit, and large, firm berries that ripen from mid-April through May when grown as a deciduous plant in north central Florida and south Georgia. Several thousand plants of 'FL06-556' have been propagated by softwood stem cuttings in Gainesville, Fla., and the resulting plants have all been phenotypically indistinguishable from the original plant. Contrast is made to 'Emerald' (U.S. Plant Pat. No. 12,165), an important variety widely planted in the southeastern United States. The claimed plant is important because it has a more upright growth habit, and has firmer, sweeter fruit than 'Emerald'. 'FL06-556' blooms later and fruit matures later than that of 'Emerald'. 'FL06-556' can be mechanically harvested with less fruit damage than 'Emerald'.

'FL06-556' originated as a seedling from a cross between 'Sweetcrisp' (U.S. Plant Pat. No. 20,027) as the female (seed) parent and 'FL98-325' (U.S. Plant Pat. No. 26,523) as the male (pollen) parent. This cross was made in Gainesville, Fla., in February 2003. The seedling was planted in a high-density field nursery in May 2004 and the first fruit were evaluated in April 2005. 'FL06-556' was first asexually propagated in Gainesville, Fla. by softwood stem cuttings. After the second year of fruiting in the field, in the spring of 2006, 'FL06-556' was propagated by softwood stem cuttings, and an experimental 15-plant test plot was established as part of a variety test at Windsor, Fla., in January 2007. Based on the growth, yield, and fruit quality of this plot, 'FL06-556' was repropagated by softwood stem cuttings and experimental test plots ranging from 5 to 50 plants were established near Arcadia, Citra, Interlachen, Haines City, and Waldo, Fla.; Homerville, Ga.; and Wilmington, N.C. These plots have been observed during flowering and ripening each year, and no mutations or off-type plants have been observed.

'FL06-556' differs from the parent 'Sweetcrisp' (U.S. Plant Pat. No. 20,027) in that 'FL06-556' is more upright, blooms later, and has larger berries. 'FL06-556' differs from the parent 'FL98-325' (U.S. Plant Pat. No. 26,523) in that 'FL06-556' is later maturing. 'FL06-556' differs from the commercial variety 'Emerald' (U.S. Plant Pat. No. 12,165), an important variety widely planted in the southeastern United States, in that 'FL06-556' has a more upright growth habit, blooms later, and has a higher chilling requirement. 'FL06-556' berries ripen later and are sweeter than 'Emerald' berries.

SUMMARY OF THE INVENTION

Blueberry variety 'FL06-556' exhibits outstanding and distinguishing characteristics when grown under normal horticultural practices in Florida, including: (1) a low chilling requirement, particularly for the flower buds; (2) a vigorous, upright growth habit; (3) later ripening (50% ripe berries in North Florida around May 5); and (4) very firm, large, sweet berries with a small, dry picking scar.

BRIEF DESCRIPTION OF THE DRAWINGS

The accompanying photographs show typical bush, flower, and fruit characteristics for 'FL06-556'. Colors shown are as true as can be reasonably reproduced by photographic procedures and may differ from those cited in the detailed description, which accurately describes the colors of 'FL06-556'.

DETAILED BOTANICAL DESCRIPTION

Figure 1:
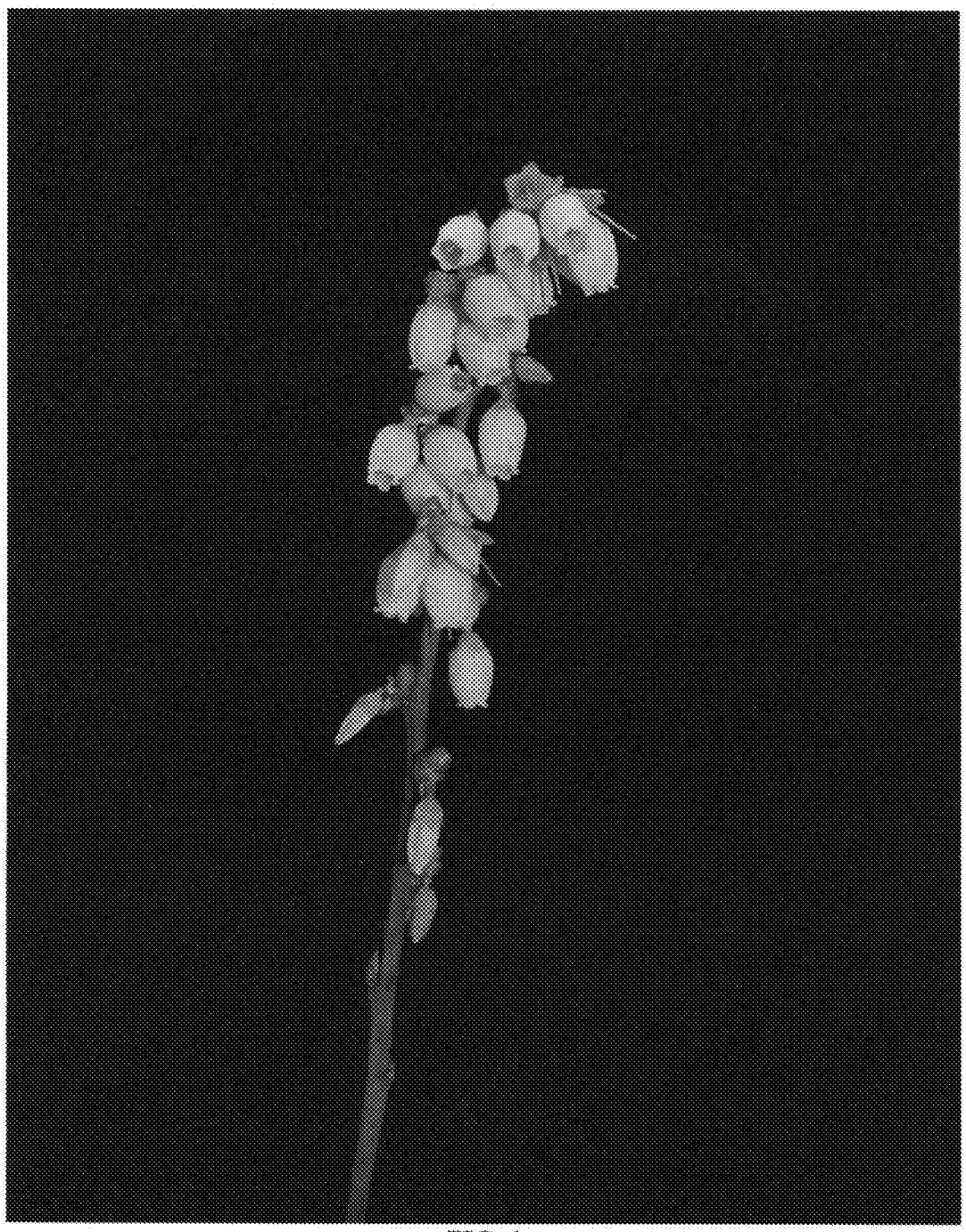
FIG. 1—Shows several clusters of opening 'FL06-556' flowers.
Figure 2:
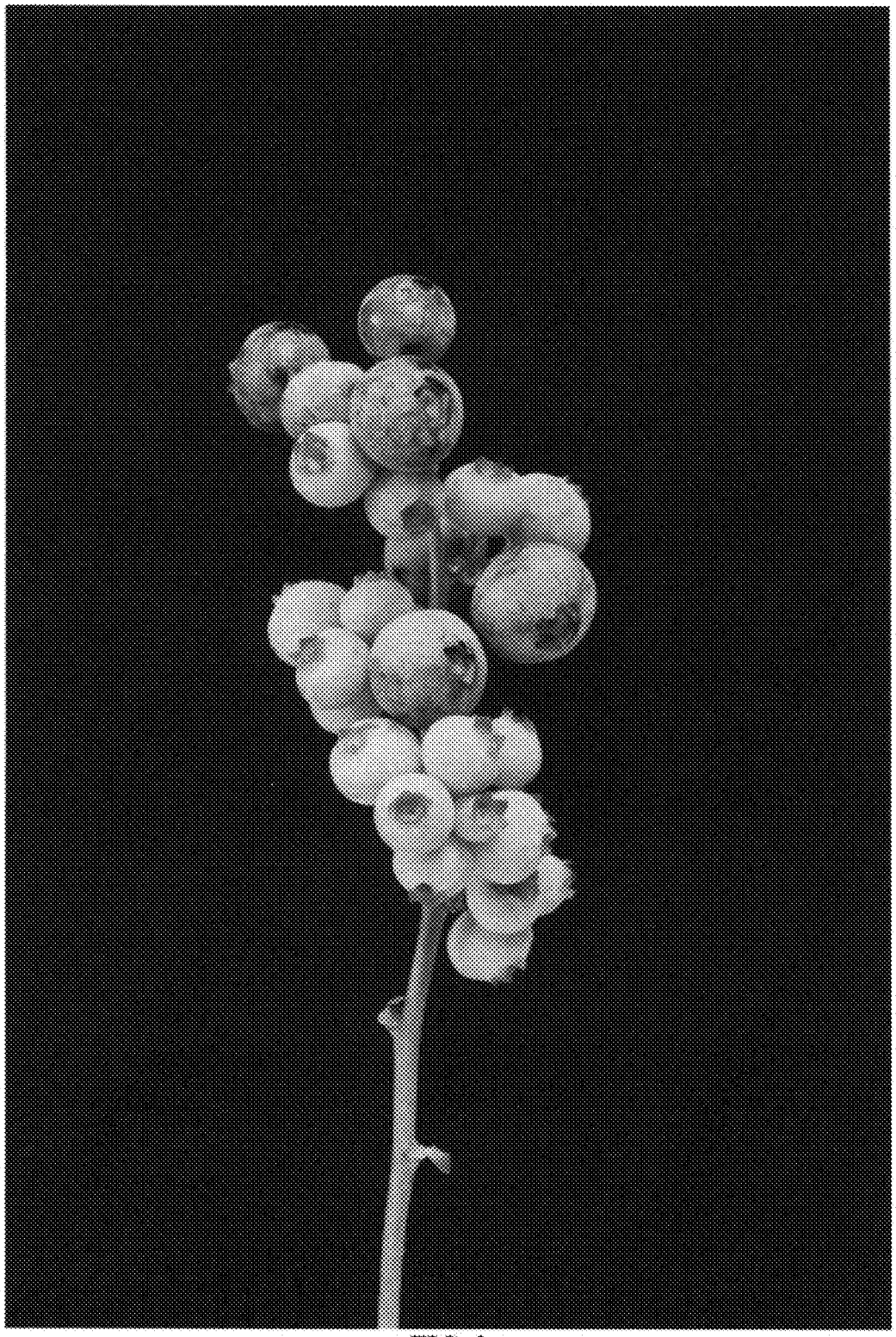
FIG. 2—Shows clusters of 'FL06-556' berries during the fruit ripening season.
Figure 3:
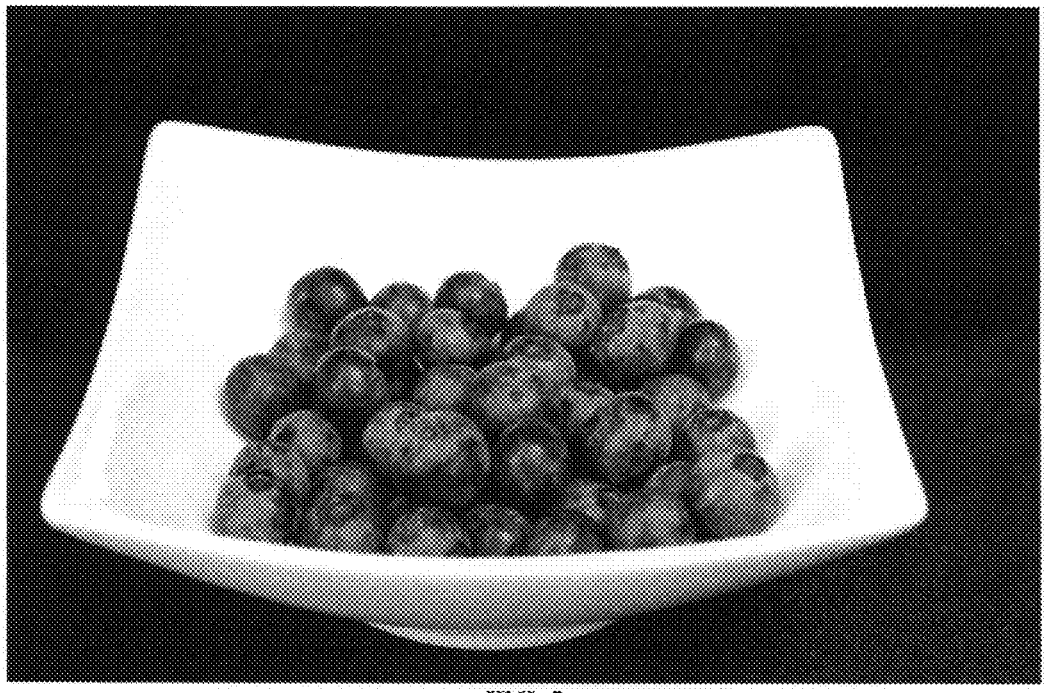
FIG. 3—Shows a close-up of harvested 'FL06-556' berries.
Figure 4:
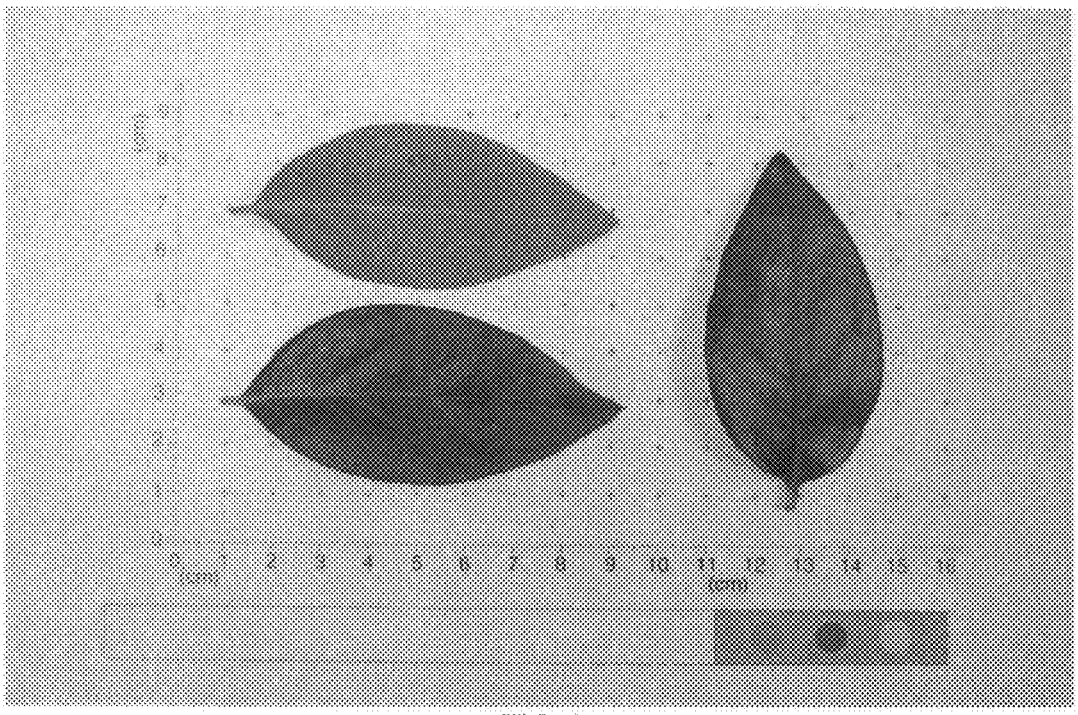
FIG. 4—Shows a close-up of mature 'FL06-556' leaves with a scale bar.
Figure 5:
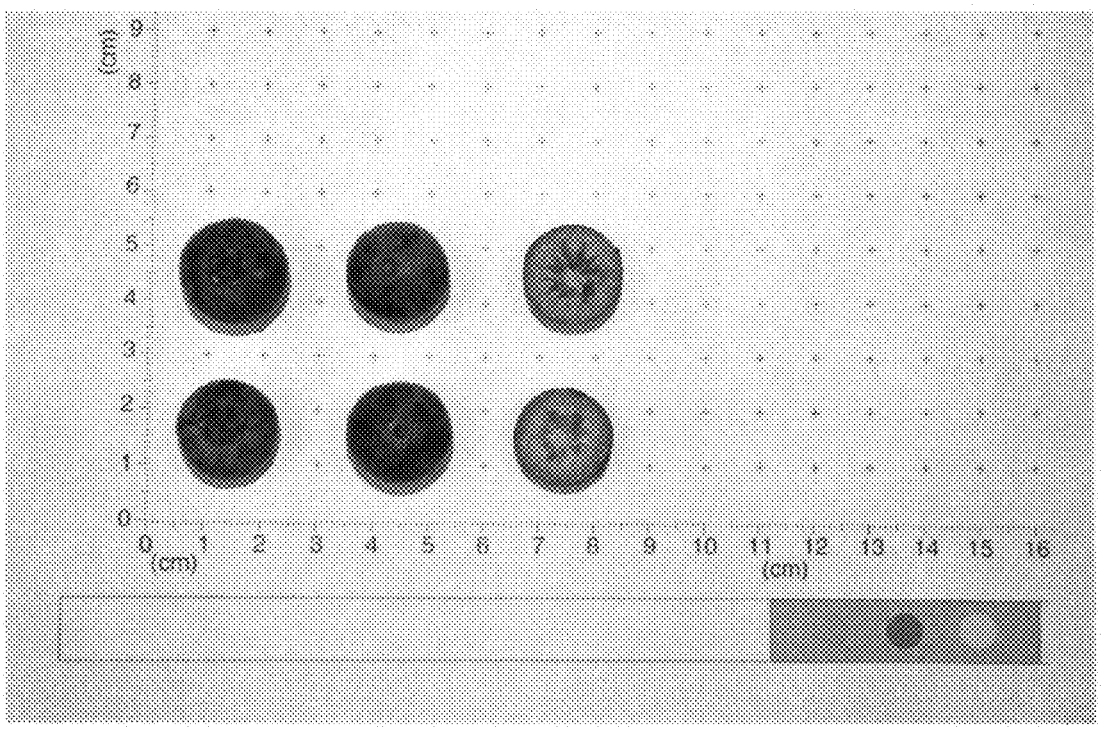
FIG. 5—Shows a close-up of mature 'FL06-556' fruit with a scale bar.
Figure 6:
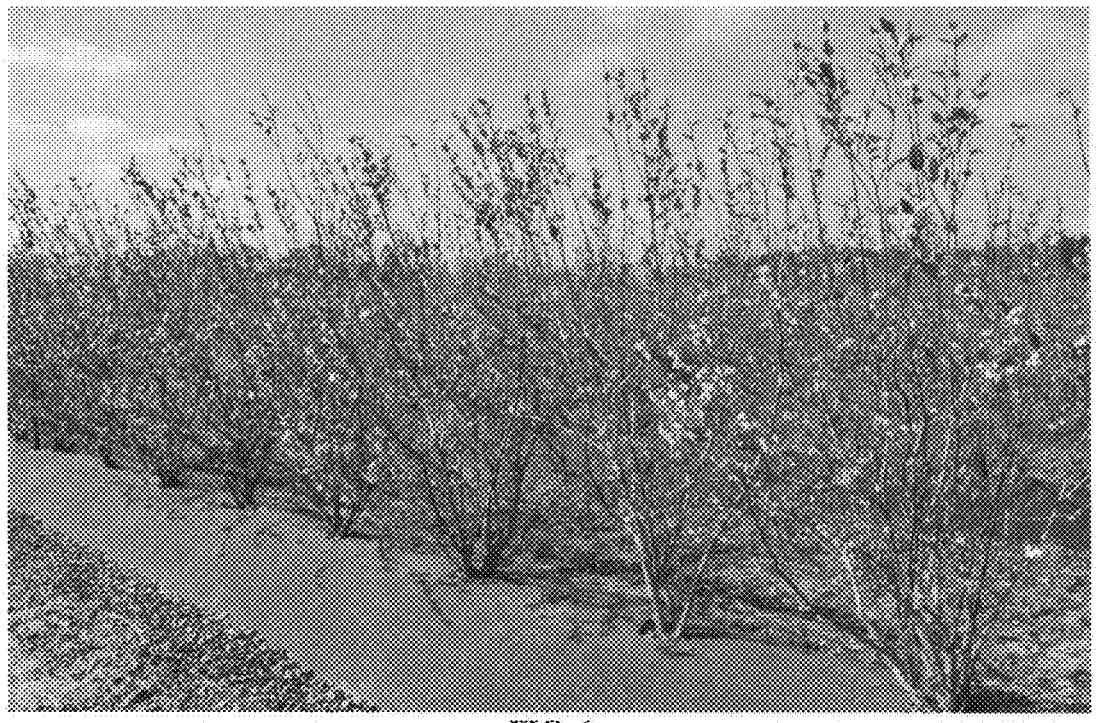
FIG. 6—Shows several three-year-old 'FL06-556' plants in February with the vigorous, upright plant architecture visible.

The following detailed description sets forth the distinctive characteristics of 'FL06-556'. The data that define these characteristics were collected from asexual reproductions carried out in Florida. The plant history was taken on a plot of 50 four-year-old plants growing in a commercial field near Waldo, Fla. Certain characteristics may vary with plant age. 'FL06-556' has not been observed under all possible environmental conditions, and the measurements given may vary when grown in different environments. Where means are given, the sample size was 20. Color descriptions are based on The Royal Horticultural Society (R.H.S.) Colour Chart by The Royal Horticultural Society, London, Fifth Edition, 2007. When the R.H.S. color designations differ from the accompanying photographs, the R.H.S. color designations are accurate.

Phenotypic Description of *Vaccinium corymbosum* L. ('FL06-556')

Plant:

- *Plant vigor*.—High. Vigor is greater than 'Emerald' (U.S. Plant Pat. No. 12,165).
- *Growth habit*.—Upright.
- *Plant height*.—2.2 m on average for 4-year old plant.
- *Plant spread*.—1.4 m on average for 4-year old plant.
- *Flower bud density (number) along flowering twigs in January*.—High.
- *Twigginess*.—Medium.
- *Tendency toward evergreenness*.—Medium.
- *Productivity*.—In northeast Florida, 'FL06-556' produces approximately 2 kg per season from plants 3 years or older.
- *Chilling requirement*.—300 hours below 7° C., 'FL06-556' has performed poorly when receiving less than 300 hours.
- *Cold hardiness*.—'FL06-556' has not been grown in temperate climates with extremely cold winter temperatures. Plants have survived winter freezes of −6° C. with minimal damage.
- *Ease of propagation*.—'FL06-556' has only been propagated from softwood stem cuttings, where the rooting percentage is greater than 70% and comparable to other varieties.

Trunk and branches:

- *Suckering tendency*.—Low. Three-year-old plants typically have 5 to 7 major canes arising from a crown 30 cm in diameter.
- *Surface texture (of strong, 6-month-old shoots observed in January)*.—Smooth.
- *Surface texture (of 3-year-old and older wood)*.—Rough.
- *Color of new twigs observed in the field*.—Yellow-green 144C.
- *Color of 3-year-old, rough-textured canes*.—Greyed-orange 177D.
- *Internode length (strong, upright shoots measured in June)*.—Mean of 12.9 mm.

Leaves:

- *Length (including petiole, from tip of petiole to end of blade)*.—Mean of 7.7 cm.
- *Width (at widest point)*.—Mean of 3.5 cm.
- *Shape*.—Elliptic, with an attenuate base and acute tip.
- *Margin*.—Entire.
- *Color*.—Upper surface: Green 139A. Lower surface: Greyed-green 191B.
- *Pubescence*.—Upper surface of leaves: Absent. Lower surface of leaves: Absent. Margins: Absent.
- *Timing of vegetative bud burst (early, medium, late)*.—Medium.
- *Relative time of leafing versus flowering*.—When not treated with hydrogen cyanamide in mid-winter, leafing occurs after flowering.

Flowers:

- *Arrangement*.—Flowers are arranged alternately along a short, leafless, deciduous branch.
- *Fragrance*.—Very slight floral fragrance.
- *Shape*.—Urceolate, and cylindrical.
- *Flowering period*.—Mean date of 50% open flowers in Waldo, Fla. is February 14; averages 10 days later than 'Emerald' (U.S. Plant Pat. No. 12,165).
- *Cluster (tight, medium, loose)*.—Medium.
- *Number of flowers per cluster*.—Mean of 6.1.
- *Pedicel*.—Length at time of anthesis: Mean of 4.8 mm. Color at time of anthesis: Yellow-green 145A with Red 47B on the sun-exposed side.
- *Peduncle*.—Length at time of anthesis: Highly variable, mean of 9.5 mm. Color at time of anthesis: Yellow-green 150C with Red 47A on sun-exposed side.
- *Calyx*.—Surface texture: Smooth. Diameter: Mean of 6.4 mm. Color (outer surface, visible at the time of anthesis without removing the corolla tube): Green 137C to Yellow-green 145B on tips of calyx lobes.
- *Corolla*.—Diameter: Mean of 7.6 mm. Length (from pedicel attachment point to corolla tip excluding the pedicel): Mean of 12.3 mm. Aperture diameter: Mean of 4.0 mm. Texture: Smooth. Color: Green-white 157D. Anthocyanin coloration in corolla tube — Absent.

Reproductive organs:

- *Style*.—Length (top of ovary to stigma tip): Mean of 10.2 mm. Color: Yellow-green N144A. Location of tip of stigma relative to lip of the corolla — Stigma tip is approximately even to 1 mm below the corolla lip.

*Anthers*.—Color: Greyed-orange 167A. Pollen — Abundance of shed: High. Pollen germination: Typically greater than 90%. Color: Yellow 11D. Filament length — 3 mm on average. Filament width — 1 mm on average.

*Self-fruitfulness*.—Low to medium. Planting in field configurations that promote cross fertilization with other southern highbush varieties is recommended for all southern highbush blueberry plants grown in Florida.

Fruit:

*Mean date of* 50% *harvest in Citra, Fla*.—May 5.

*Diameter of calyx aperture on mature berry*.—Mean of 5.5 mm.

*Size and shape of calyx lobes on mature berry*.—Very small, erect to incurving. Shallow calyx basin.

*Pedicel length on ripe berry*.—Mean of 7.0 mm.

*Detachment force for ripe berries*(*easy, medium, hard*).—Easy.

*Fruit cluster density* (*sparse, medium, dense*).—Medium.

*Number of berries per cluster*.—Mean of 5.0.

*Fruiting type*.—On one-year-old and current season's shoots.

Berry:

*Cluster* (*tight, medium, loose*).—Loose.

*Weight* (*on well-pruned plants*).—Mean of 2.5 g.

*Height*.—Mean of 14.5 mm.

*Width*.—Mean of 17.6 mm.

*Shape*.—Round.

*Surface color of mature berries ripe on the plant*.—Violet-blue 98C.

*Intensity of fruit bloom*.—Medium.

*Surface color of ripe berry after polishing*.—Black 203C.

*Immature berry color, with bloom*.—Greyed-green 191C.

*Immature berry color without bloom*.—Yellow-green 146B.

*Flesh color*.—NN 155 A.

*Surface wax*.—Medium to high. The surface wax on 'FL06-556' has only medium persistence.

*Pedicel scar*.—Small and dry. Mean of 1.8 mm.

*Firmness*.—Very firm.

*Flavor*.—Sweet, low acid.

*Intensity of fruit sweetness*.—Medium.

*Texture*.—Crisp, crunchy, medium seeds, and no stone cells present.

*Fruit storage quality*.—Fruit is unusually firm and can be stored without shriveling, mold, or loss of firmness for 4 weeks or more at 2° C.

Seeds:

*Color of dried seeds*.—Greyed-orange 165B.

*Weight of well-developed dried seed*.—Mean of 0.7 mg.

*Length of well-developed dried seed*.—Mean of 1.9 mm.

*Width of well-developed dried seed*.—Mean of 1.2 mm.

Use: 'FL06-556' produces southern highbush blueberries suitable for both the fresh and processed fruit markets.

Resistance to diseases, insects, and mites: 'FL06-556' has grown vigorously and shows excellent bush survival in the field. It appears to be tolerant to stem blight (*Botryosphaeria* spp.) and root rot (*Phytophthora cinnamoni*), with very few young plants dying soon after planting. The reaction of 'FL06-556' to the various fungal species that cause summer leaf spots is typical of other southern highbush varieties, and fungicide applications may be needed after harvest to reduce foliar diseases and retain leaves into the fall for maximum flower bud set. Similarly, susceptibility to typical blueberry insect and mite pathogens such as spotted wing *drosophila* (*Drosophila suzukii*), blueberry gall midge (*Dasineura oxycoccana*) and blueberry bud mite (*Acalitus vaccini*) is similar to other southern highbush cultivars.

What is claimed is:

1. A new and distinct variety of southern highbush blueberry plant named 'FL06-556', as illustrated and described herein.

* * * * *